United States Patent [19]

Moro

[11] Patent Number: 5,218,312

[45] Date of Patent: Jun. 8, 1993

[54] MEASUREMENT APPARATUS FOR MEASURING A BIOLOGICAL SUBSTANCE WITHIN A FLUID SUBSTRATE

[76] Inventor: Ricardo Moro, 14601 134th Ave., Edmonton, Alberta, Canada, T5L 4S9

[21] Appl. No.: 826,263

[22] Filed: Jan. 24, 1992

Related U.S. Application Data

[63] Continuation of Ser. No. 221,585, Jul. 20, 1988, abandoned.

[51] Int. Cl.⁵ ..................... G01R 27/22; G01N 27/06
[52] U.S. Cl. .................................. 324/711; 324/710; 324/692; 324/444; 422/82.02
[58] Field of Search .................... 324/692, 71.1, 693, 324/710, 711, 722, 444, 442; 422/82.02

[56] References Cited

U.S. PATENT DOCUMENTS

| | | | |
|---|---|---|---|
| 3,316,896 | 5/1967 | Thomasset | 324/692 X |
| 3,890,201 | 6/1975 | Cady | 324/692 |
| 3,963,984 | 6/1976 | Coulter | 324/71.1 |
| 4,072,578 | 2/1978 | Cady et al. | 204/403 |
| 4,225,410 | 9/1980 | Pace | 435/817 |
| 4,230,983 | 10/1980 | Steere et al. | 324/71.1 |
| 4,362,988 | 12/1982 | Weimar | 324/711 X |
| 4,713,347 | 12/1987 | Mitchell et al. | 435/291 |
| 4,801,546 | 1/1989 | Ackland | 324/71.1 |
| 4,920,047 | 4/1990 | Giaever et al. | 435/817 |

FOREIGN PATENT DOCUMENTS

| | | | |
|---|---|---|---|
| 0826790 | 11/1969 | Canada | 324/711 |
| 0746332 | 7/1980 | U.S.S.R. | 324/711 |
| 0781709 | 11/1980 | U.S.S.R. | 324/711 |

OTHER PUBLICATIONS

Siggaard-Andersen, M. D., Ph.D., "Electrochemistry", 18-Analytical Procedures and Instrumentation, p. 110. Dec.-1990.

Gosling, "A Decade of Development in Immunoassay Methodology", Clinical Chemistry, vol. 36, No. 8, Dec. 1990, pp. 1408-1427.

Frew et al, "Potentiometric and Amperometric Immunoassays", Complementary Immunoassays, pp. 209-225. Dec. 1988.

Wehmeyer et al, "Heterogeneous Enzyme Immunoassay with Electrochemical Detection: Competitive and 'Sandwich'-Type Immunoassays", Clinical Chemistry, vol. 31, No. 9, Dec. 1985, pp. 1546-1549.

Stanley et al, "Amperometric Enzyme-Amplified Immunoassays", Journal of Immunological Methods, 112 (Dec. 1988) pp. 153-161.

*Primary Examiner*—Jack B. Harvey
*Attorney, Agent, or Firm*—Litman, McMahon & Brown

[57] ABSTRACT

A method and apparatus for performing an enzyme-linked immuno sorbent assay of a biological substance in a fluid substrate wherein an enzyme conjugate is used to react with the biological substance to cause the release of ions into the substrate. The change in the resistivity of the substrate due to the release of ions is measured, and an analog signal is generated in response thereto. The analog signal is converted into a digital signal, which is quantized and output in a human readable form for indicating the quantity of the biological substance present in the substrate.

6 Claims, 5 Drawing Sheets

MEASUREMENT APPARATUS FOR MEASURING A BIOLOGICAL SUBSTANCE WITHIN A FLUID SUBSTRATE

This application is a continuation of application U.S Ser. No. 07/221,585, filed Jul. 20, 1988, now abandoned.

FIELD OF THE INVENTION

The present invention relates to a method and apparatus for the detection of organic substances, and more particularly relates to an improved ELISA reader for detecting trace amounts of biological substances in a sample.

BACKGROUND OF THE INVENTION

ELISA (Enzyme Linked Immuno Sorbent Assay) test procedures have been developed for the detection of organic substances in blood and other bodily and biological fluids.

The ELISA technique is based upon three primary principles; first, the ability of proteins to bind to plastic; the high affinity and specificity of antigen/antibody reactions and the ability of enzymes to modify a substrate. ELISA assay procedures are well known, and will not therefore be described in great detail herein. Briefly however, a plastic plate having typically 96 individual plastic wells is the receptacle for the fluid sample. Each of the 96 wells is coated with an antibody and an antigen specific to the antibody is bound thereto to hold the antigen in place. A second antibody specific to the same antigen is added and bonded thereto. The second antibody has been covalently conjugated prior to its introduction with an enzyme which will react with a substrate to cause a colour change therein given the right environmental conditions. The degree of colour change in the substrate is proportional to the amount of the biological substance such as an antigen sought to be detected. By passing filtered light through the substrate and measuring its degree of absorption by the substrate using an ELISA reader, one can calculate the concentration of the biological substance therein as a function of the amount of absorbed light, which is assigned a numerical value or index. The greater the colour intensity of the substrate, the greater the absorption of light.

The use of ELISA techniques has increased greatly having regard to the procedure's relative simplicity, speed, reliability, sensitivity and as a means of avoiding the use of radioactive assays.

The disadvantages of ELISA readers that measure light absorption are several. The readers themselves are delicate and sensitive and require constant adjustment to maintain optimal sensitivity. The linear response of the readers falls within a very narrow range so that each test requires large numbers of dilutions so that at least one or two of such dilutions falls within the linear range of the instrument. A relatively intense light source is required making it more difficult to obtain a portable unit having regard to the inherent power requirements of the system, and of course the plastic lens at the bottom of each well must pass the light without distortion, necessitating the use of relatively expensive optical grades of plastic which further adds to the costs. The readers themselves are relatively expensive (prices range from $6000. for relatively simple models, up to $28,000. for units with computerized data management and analytical capabilities) and some existing readers perform only one light measurement at a time, making the reading of a 96 well plate a relatively time-consuming process.

SUMMARY OF THE INVENTION

It is an object of the present invention to obviate and mitigate the disadvantages of existing ELISA readers and provide an improved reader of equal or greater sensitivity which is faster to use, requires less maintenance and energy, possesses greater linearity, is less costly to build and is more amenable to the construction of a portable unit.

In accordance with these objects, it has been found advantageous to produce an analyzer reader that measures not light absorption, but rather the conductivity or conversely, the resistivity or the impedance of the substrate following enzymatic reaction. As will therefore be appreciated, the present invention contemplates the use of enzyme conjugates which promote the formation of ions in the substrate, rather than colour reactions. One such conjugate uses urease which catalyzes the transformation of urea into ammonium carbonate. The ammonium is present in the substrate in the form of ions which change the conductivity/resistivity of the substrate. This change can be measured and is directly proportional to the amount of biological material present in the substrate that is to be measured. Quantifying the change will produce a measurement of the biological substance useful to the tester. Because the power requirements for the proposed system are very low, the development of a portable unit is greatly facilitated.

According to the present invention, then, there is provided in a method of performing an enzyme-linked immuno sorbent assay of a biological substance in a substrate, the improvement comprising utilizing an enzyme conjugate to react with the biological substance to cause the release of ions into the substrate, measuring the change in resistivity of the substrate due to the presence of the ions, generating an analog signal in response to the measurement of resistivity, converting the analog signal into a digital signal, and quantizing the digital signal and outputting the same in human readable form for indicating the quantity of the biological substance present in the substrate.

According to a further aspect of the present invention, there is also provided apparatus for performing an enzyme-linked immuno sorbent assay of a biological substance in a fluid substrate, comprising means for measuring the resistivity of the substrate and producing an analog signal representative thereof, converter means for converting the analog signal into a digital signal, and processing means to process the digital signal to produce numerical data indicative of the quantity of the biological substance in the substrate.

BRIEF DESCRIPTION OF THE DRAWINGS

Preferred embodiments of the invention will now be described in greater detail, and will be better understood when read in conjunction with the following drawings, in which.

DETAILED DESCRIPTION OF PREFERRED EMBODIMENTS

The basic ELISA test procedure described above for colourmetric measurement is followed in the present instance with the exception that the enzyme conjugate used to induce colour reactions (usually peroxidase antibody or alkaline phosphatase) is replaced with, for example, a urease conjugate for transforming urea into ammonium carbonate. The presence of ammonium ions in the substrate raises its pH, which can be detected using well known techniques, but this provides only a visual confirmation of the presence of the ions without a quantitative measurement of concentrations. The other change in the substrate is as aforesaid to its resistivity/conductivity which can be measured in a quantitative sense. Both urea and pure water are highly resistive, such that a change in conductivity is directly related to the concentration of ammonium ions in solution which in turn is a function of the amount of biological material present to be measured. The use of other conjugates for detecting different substances but which nevertheless transform a non-ionized substrate into one which is of course contemplated, and the foregoing and subsequent descriptions relating to the use of urease are intended to be exemplary in nature only.

Figure 1:
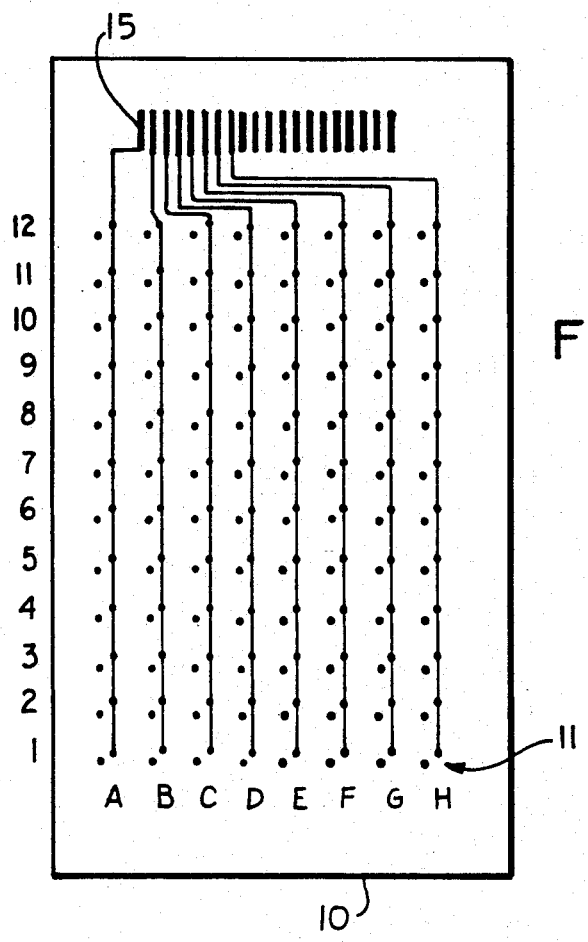
FIG. 1 is a bottom plan view of a two-pin electrical probe forming part of the proposed ELISA reader.
Figure 2:
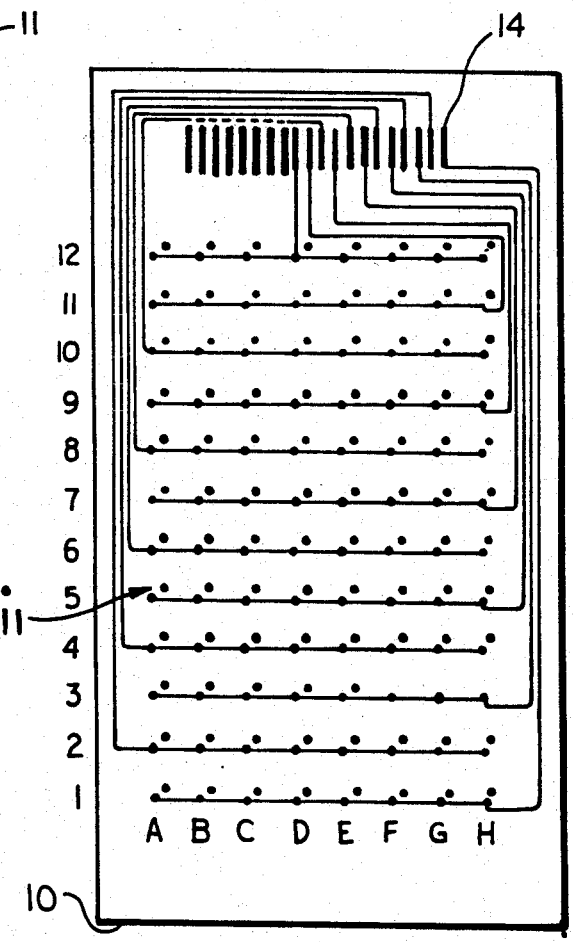
FIG. 2 is a top plan view of the probe of FIG. 1.

With reference now to FIGS. 1 and 2, there is shown an electrical probe 10 having 96 pairs of conductive pins or electrodes 11 corresponding to the 96 wells on the plastic plate (not shown). The pairs of pins 11 are arranged into twelve columns 1–12 and eight rows A–H, with the pins in each column being connected in parallel and thence to one of electrical contacts 14 as shown in FIG. 2, and the pins of each row being similarly connected together and thence to an electrical contact 15 as shown in FIG. 1. By switching between a pair of contacts consisting of one of contacts 14 and one of contacts 15, each of the 96 pin pairs 11 can be individually selected.

Figure 3:
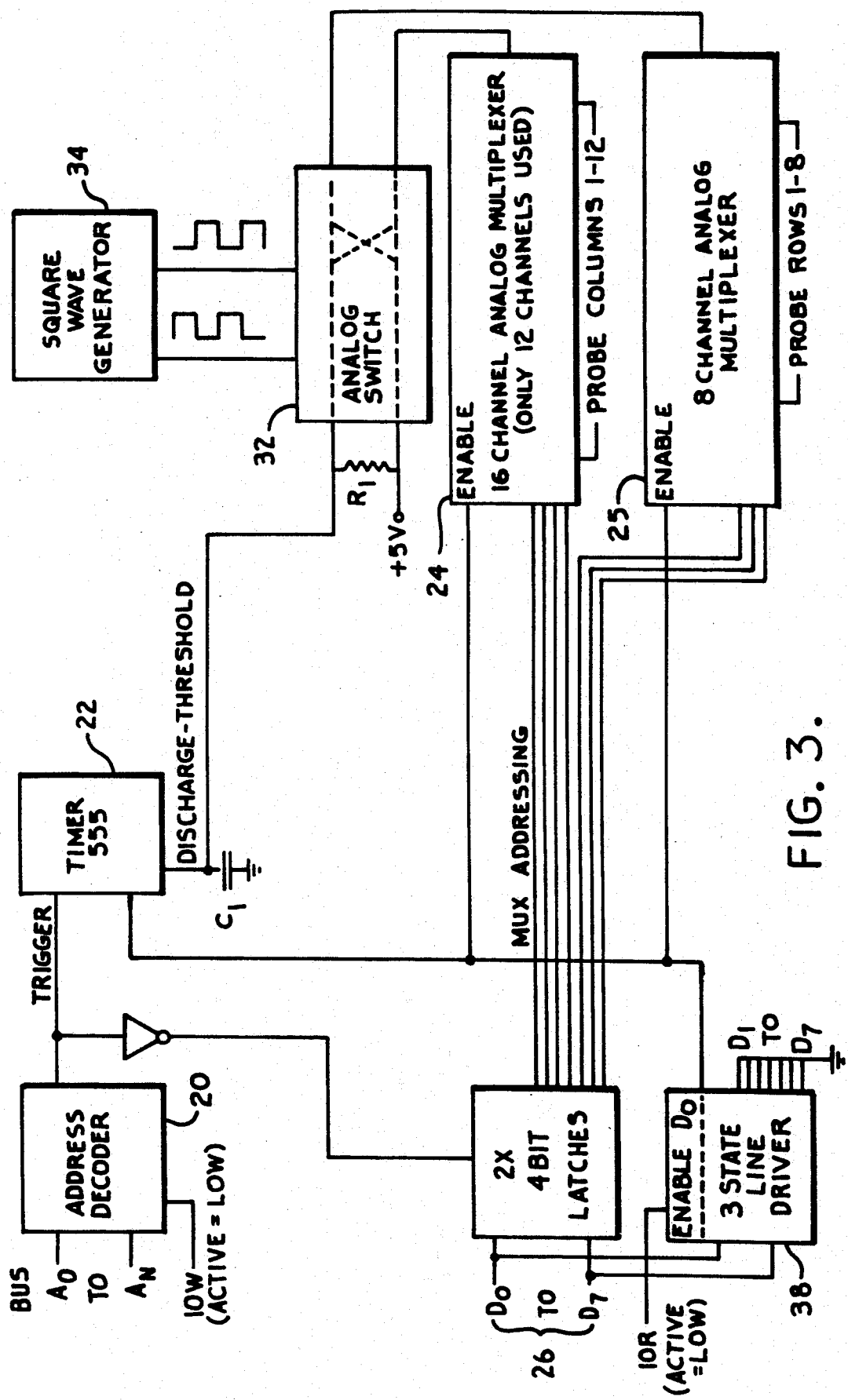
FIG. 3 is a block circuit diagram of a computer-based ELISA reader in accordance with one aspect of the present invention.
Figure 4:
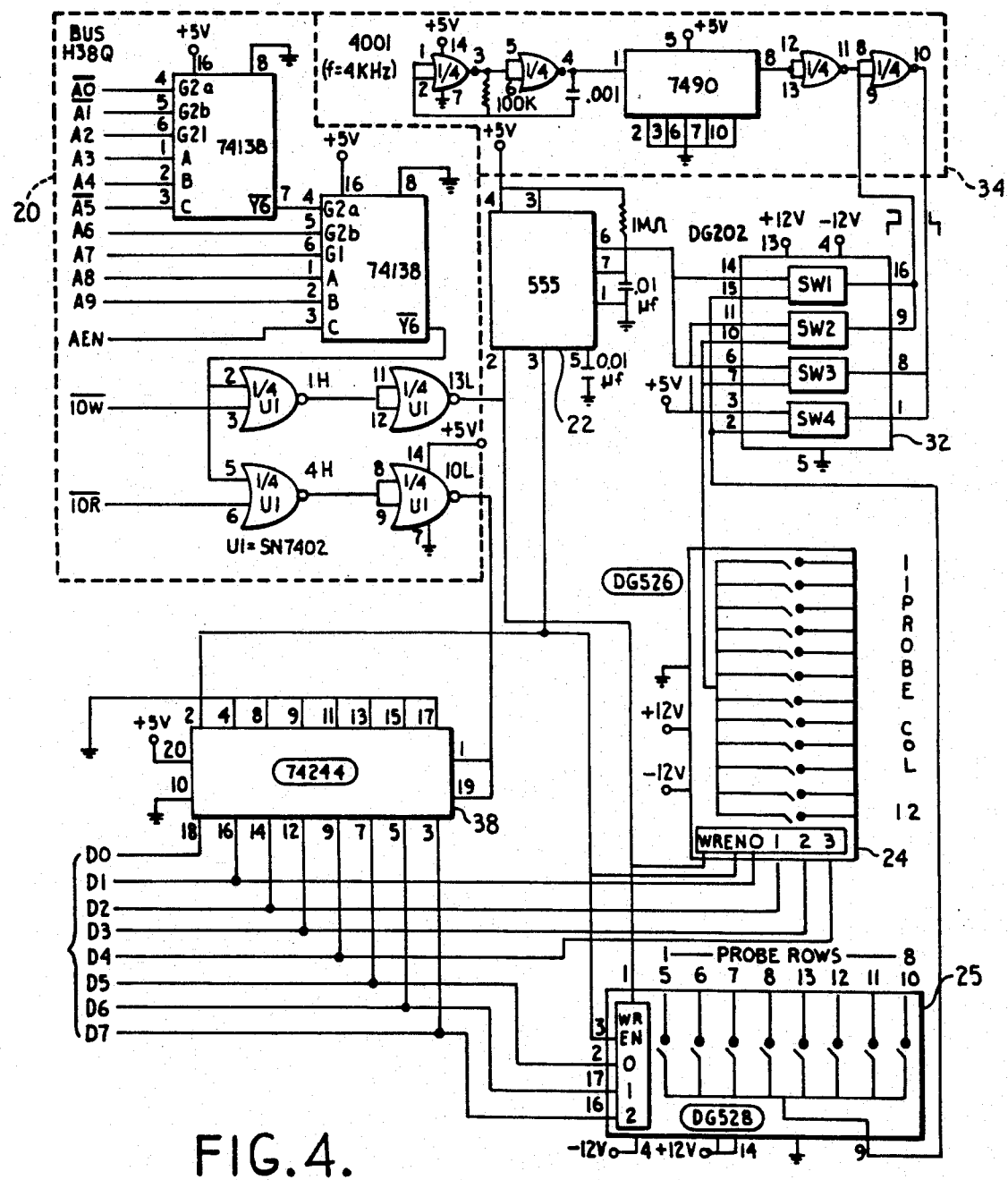
FIG. 4 is a schematic diagram of the ELISA reader card circuit for computer installation.

In one embodiment of the invention as contemplated by the applicant, the switching between pin pairs and data acquisition is computer-implemented. The computer-based reader card is illustrated schematically with reference to FIGS. 3 and 4. An IBM XT ™ or compatible computer may be used for this purpose and the card may be plugged into one of the expansion slots therein for direct input of the data into the computer.

Probe 10 is placed in contact with the plastic well plate so that each of pin pairs 11 can measure the resistivity of the solution in its respective well, this resistivity being a function, as aforesaid, of the presence of ammonium carbonate ions released into solution as a result of the enzymatic reaction.

The computer itself is programmed to sample and analyze the data whereby each of the pairs of electrodes 11 is sequentially connected to an analog/digital converter through an electronic inverting switch which prevents polarization of the electrodes. On command, address decoder 20, comprising two 74138 and one 7402 integrated circuits, is activated. In writing mode with the IOW terminal active, timer 22 is activated to enable multiplexers 24 and 25, both of which are latched to the data on the input bus 26 by the IOW instruction. The bus data determines the pair of pins 11 on probe 10 to be read with multiplexer 24 selecting one of columns 1 to 12, and multiplexer 25 selecting one of designated rows A to H. Analog switch 32 connected to both of the multiplexers flips the polarity of pins 11 at a rate of approximately 700 Hz to prevent potentially deleterious sustained polarization of the electrodes. Switch 32 is itself pulsed to flip the polarity of the electrodes by means of a square wave generator 34 which produces the 700 Hz signal required for this purpose.

The analog resistivity measurement taken by the pairs of pins determines the time period that the output of timer 22 is high. That is, the duration of the timer's output signal is determined by the resistivity of the solution in the measured well. The output is connected to a three-state line driver 38 (a 74244 IC) which outputs a digital signal to bus 26. When the time is on, the data on input bus 26 will be 00000001 which value is read in accordance with the computer program which activates the driver through an IOR command to allow the computer to read the number on bus 26. If the number on the bus is 1, the program remains in a loop which subtracts one unit to a preset variable. Accordingly, when the number on the bus equals 0, the program exits and the variable's value will be directly proportional to the resistance of the substrate. The presence of a relatively large number of ammonium ions will of course decrease the resistance of the substrate and will cause a small decrease in the variable's initial value. Conversely, a weak reaction will cause more loops to decrease the variable's initial value to produce a smaller final value. The values so produced are outputted in some useful human readable form or stored in memory for subsequent analysis.

Figure 5:
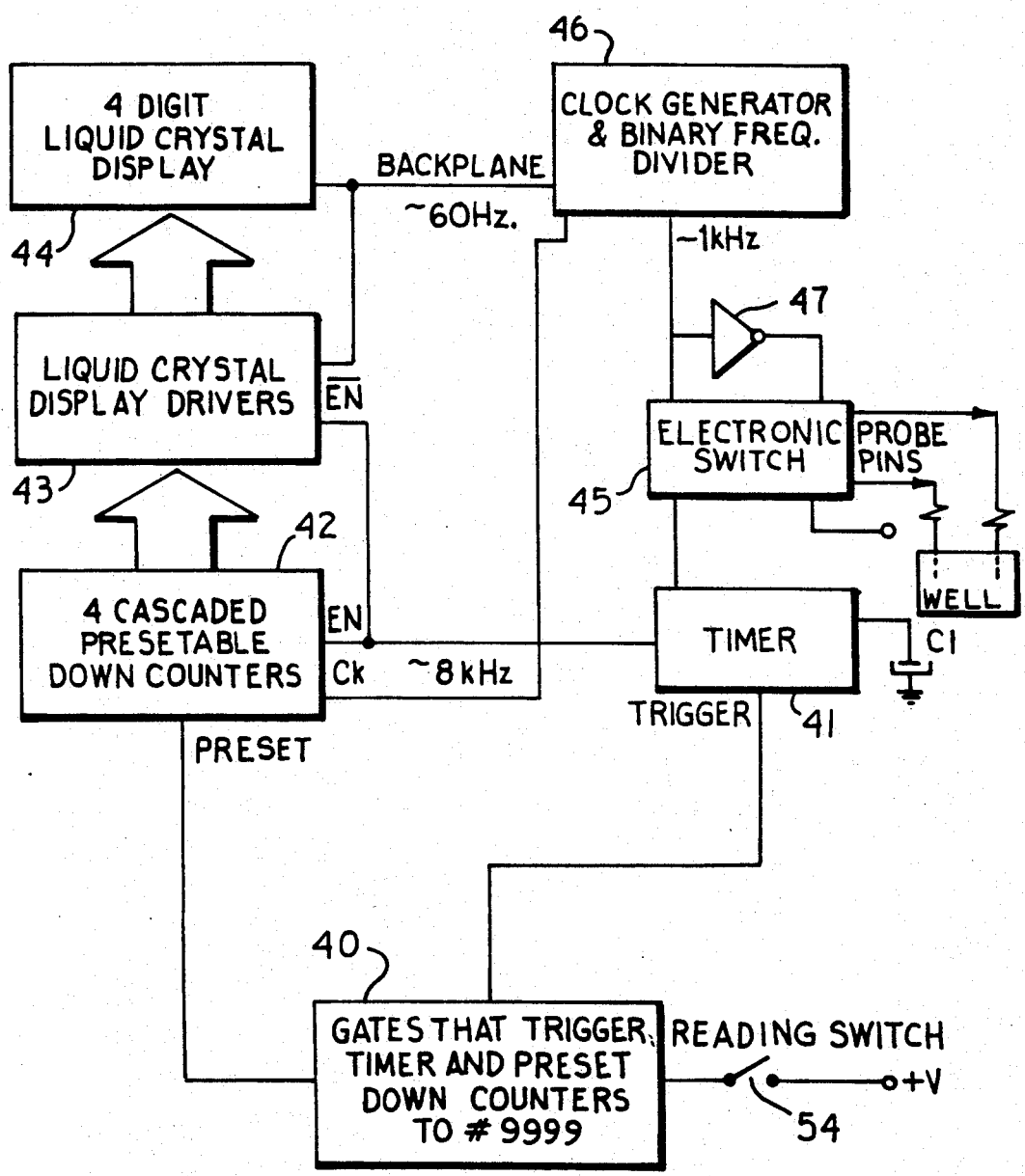
FIG. 5 is a block circuit diagram for a portable/hand held ELISA reader in accordance with another aspect of the present invention.
Figure 6:
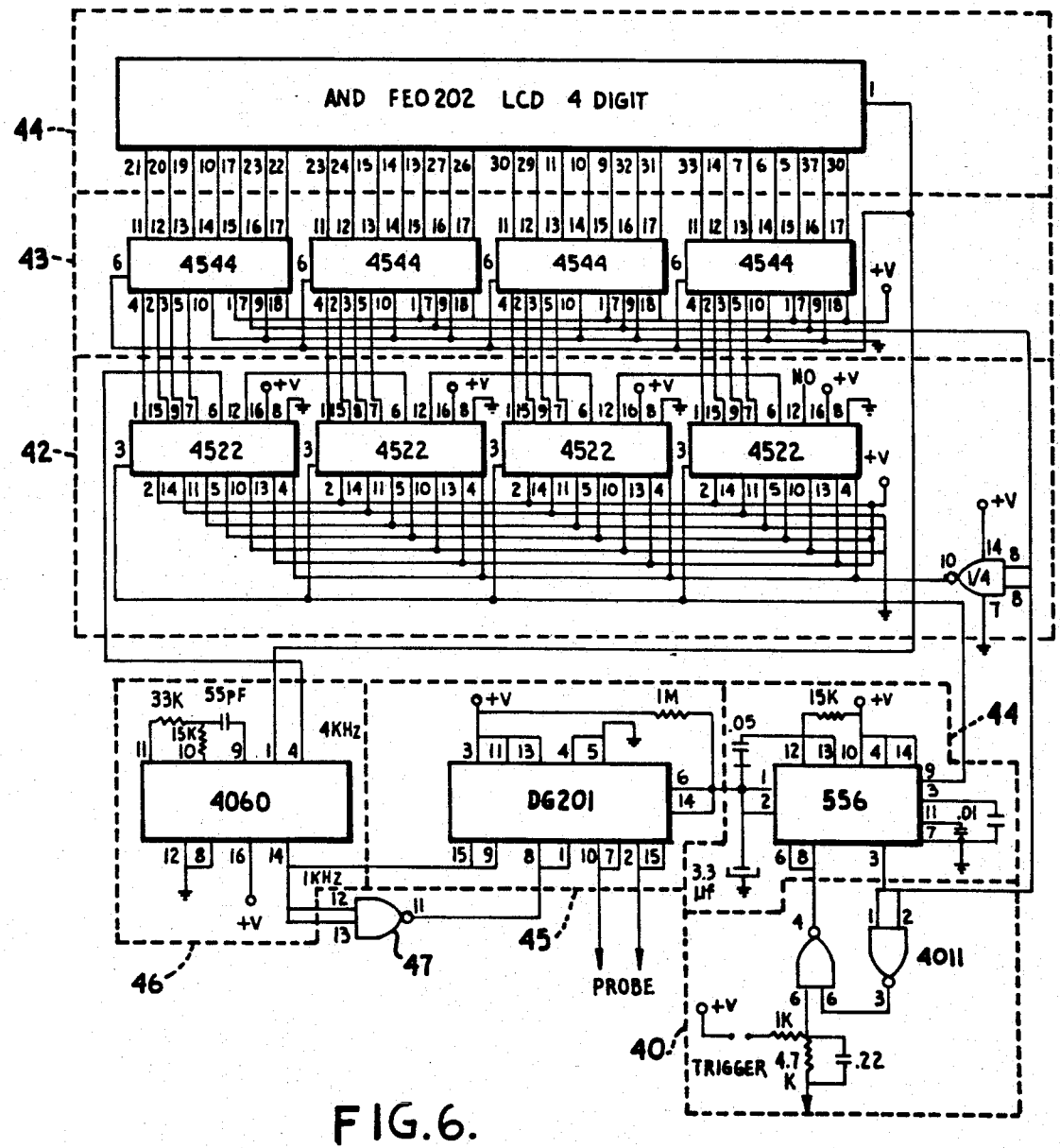
FIG. 6 is a schematic diagram of the portable reader of FIG. 5.

The low power requirements of the present method and apparatus facilitate the development of a hand-held unit for portable operation. The circuitry for such an apparatus will now be described with reference to FIGS. 5 and 6.

A suitable two-pin electrical probe (not shown) is immersed in the well to be measured, the probe being shaped to fit the well as required. The measurement is initiated by closing a switch 54 referred to as a reading switch, which triggers logic gate unit 40 to deliver a LOW output signal to a timer 41 and a HIGH output signal to a group of cascaded presettable downcounters 42. Downcounters 42 are preset by the HIGH signal to a predetermined number such as 9999. Timer 41 is actuated by the LOW signal from gates 40 to deliver a HIGH signal of its own to downcounters 42 which begins to count down from 9999. The same HIGH signal from timer 41 simultaneously disables display drivers 43 to turn LCD display 44 off during the reading period. When the reading has been completed, the timer's LOW signal deactivates the downcounters and reactivates drivers 43 and hence LCD 44 to display the values present at the outputs of downcounters 42.

The time interval that drivers 43 are disabled by timer 41 is related to the resistance of the sample being measured in the well in which the electrodes of the probe are immersed, and the value of capacitor C1. When drivers 43 are disabled, downcounters 42 count down the pulses from an 8 KHz clock generator 46. If the reaction in the well is strong and a relatively large number of ions are released into solution, the resistivity of the substrate will be low and the signal from timer 41 will disable drivers 43 and enable downcounters 42 for a relatively short period of time. The number of downcounted pulses from clock generator 46 will be relatively few and consequentially, the number output on LCD 44 will be large. Conversely, if relatively few ions are released into solution whereby its resistivity will be relatively high, timer 41 will disable drivers 43 and enable downcounters 42 for a proportionately longer period of time, with the result that a greater number of pulses from clock generator 46 will be downcounted to produce a lower numerical reading on LCD 44. The response of the portable reader is linear so that the reading on LCD 44 will be directly proportional to the strength of the enzymatic reaction producing ions which of course is a function of the relative concentration of the particular biological substance being tested for.

Once again, it is important that no sustained polarization of the electrodes immersed in the substrate occurs. The voltage across the electrodes is therefore inverted at a rate of approximately 1 KHz by means of electronic switch 45 driven directly by clock generator 46 or indirectly by the clock generator through an invertor 47 to alternately invert the connection of the pins to timer 41 and the voltage +V.

Clock generator 46 provides a further 60 Hz to drive the backplane of LCD 44.

As contemplated by the applicant, the portable reader can be constructed to read the 96 wells of a standard plate one at a time, or in multiples of up to and including all 96 wells.

As will be appreciated, the present method and apparatus are adapted to quantitatively measure immunological reactions other than those induced by enzymatic reactions, but wherein as a result of the reactions, ions are released into solution. Examples include the hybridization reaction between a natural nucleic acid with another natural or artificial nucleic acid, a hapten-antibody reaction or a biotin-avidin/strepto-avidin reaction.

As will be appreciated by those skilled in the art, the hand held probe may be adapted to contain a multiplexing device for the selection of respective pin pairs, a processing unit to be used, for example, to generate an output of actual concentrations or other useful data, and even a miniature printer for output of the measured data on paper.

As will be apparent to those skilled in the art, various modifications may be made in the above-described method and apparatus. It is to be understood therefore that the invention may be varied within the scope of the claims appended hereto.

The embodiments of the invention in which an exclusive property or privilege is claimed are defined as follows:

1. Measurement apparatus for measuring the amount of a biological substance in a fluid substrate wherein the presence of the biological substance alters the resistivity/conductivity of the fluid substrate in a manner which is generally proportionate to the amount of the biological substance in said fluid substrate, comprising;
   fluid substrate holding means for receiving the fluid substrate;
   electrode means for placement in said fluid substrate holding means and being operably immersible in said substrate, said electrode means and said substrate forming an impedance means with a resistance value corresponding to the resistance/conductivity of said substrate;
   timer means operably linked to said impedance means, said timer means generating a first signal and a second signal, said first and second signals being separated by a time period which is proportionate to said resistance value;
   pulse generating means for producing a series of pulses at a steady predetermined rate;
   counter means linked to said pulse generating means and enabled by said first signal and disabled by said second signal for counting all of the pulses produced between said first and second signals and producing an output indicative of the sum of the pulses;
   display means linked to said counter means and operably displaying the output of said counter means with the output of said counter means being proportionate to the original concentration of said biological substance in said substrate; and
   trigger means linked to said timer means and said counter means and being actuable to produce a first gate signal to activate said timer and a second signal to preset said counter means.

2. The apparatus of claim 1 including capacitor means connected to said timer means, said capacitor means and said impedance means forming an RC network, the value of said R C network determining the length of said time period between said first and said second signals generated by said timer means.

3. The apparatus of claim 2 wherein said counter means comprise a plurality of downcounters.

4. The apparatus of claim 2 including switch means operably linked to said electrode means for reversing the polarity of said electrode means at a predetermined rate.

5. The apparatus of claim 4 further including processor means linked to said counter means and receiving the output from said counter means for processing the output of said counter means.

6. Measurement apparatus for measuring the amount of a biological substance in a fluid substrate wherein the presence of the biological substance alters the resistivity/conductivity of the fluid substrate in a manner which is generally proportionate to the amount of the biological substance in said fluid substrate, comprising;
   fluid substrate holding means for receiving the fluid substrate;
   electrode means for placement in said fluid substrate holding means and being operably immersible in said substrate, said electrode means and said substrate forming an impedance means with a resistance value corresponding to the resistance/conductivity of said substrate;
   means operably linked to said electrode means for reversing the polarity of said electrode means at a predetermined rate;
   timer means operably linked to said impedance means, said timer means generating a first signal and a second signal, said first and second signals being separated by a time period which is proportionate to said resistance value;
   capacitor means connected to said timer means, said capacitor means and said impedance means forming an RC network, the value of said RC network determining the length of said time period between said first and said second signals generated by said timer means
   pulse generating means for producing a series of pulses at a steady predetermined rate;

counter means comprising a plurality of downcounters linked to said pulse generating means and enabled by said first signal and disabled by said second signal for counting all of the pulses produced between said first and second signals and producing an output indicative of the sum of the pulses;

processor means linked to said counter means and receiving the output from said counter means for processing the output of said counter means;

display means linked to said counter means and operably displaying the output of said counter means with the output of said counter means being proportionate to the original concentration of said biological substance in said substrate; and trigger means linked to said timer means and said counter means and being actuable to produce a first gate signal to activate said timer and a second signal to preset said counter means.

* * * * *